United States Patent [19]

Holtman

[11] Patent Number: 4,501,586
[45] Date of Patent: Feb. 26, 1985

[54] ABSORBENT STRUCTURE WITH RESERVOIR

[75] Inventor: Dennis C. Holtman, Flemington, N.J.

[73] Assignee: Personal Products Company, Milltown, N.J.

[21] Appl. No.: 474,396

[22] Filed: Mar. 11, 1983

Related U.S. Application Data

[63] Continuation-in-part of Ser. No. 207,524, Nov. 17, 1980.

[51] Int. Cl.³ .............................................. A41B 13/02
[52] U.S. Cl. ...................................... 604/380; 604/385
[58] Field of Search ................ 604/358, 385, 346–348, 604/354, 379, 368, 380

[56] References Cited

U.S. PATENT DOCUMENTS

| | | | |
|---|---|---|---|
| 2,690,749 | 10/1954 | Nelson | 604/398 |
| 3,065,751 | 11/1962 | Gobbo, Sr. et al. | 604/375 |
| 3,430,629 | 3/1969 | Murphy | 604/372 |
| 3,736,931 | 6/1973 | Glassman | 604/385 |
| 3,741,212 | 6/1973 | Schutte | 604/375 |
| 3,749,627 | 7/1973 | Jones, Sr. | 604/370 |
| 3,897,784 | 8/1975 | Fitzgerald | 604/374 |
| 4,285,342 | 8/1981 | Mesek | 604/375 |
| 4,333,462 | 6/1982 | Holtman et al. | 604/368 |
| 4,333,463 | 6/1982 | Holtman | 604/368 |

*Primary Examiner*—C. Fred Rosenbaum
*Assistant Examiner*—Sherri E. Vinyard
*Attorney, Agent, or Firm*—Martha A. Michaels

[57] ABSTRACT

The present invention provides an absorbent structure comprising a moisture-impermeable backing, an absorbent batt and a moisture-permeable cover covering at least the side opposite the moisture-impermeable backing. The absorbent batt is of loosely-compacted, cellulosic fibers and is provided with a reservoir having a capacity of at least 10 cc. The reservoir is formed by compression of the fibers in the reservoir zone and is located so that the product, when worn, retains the proper shape.

6 Claims, 5 Drawing Figures

ABSORBENT STRUCTURE WITH RESERVOIR

This application is a continuation-in-part of copending application Ser. No. 207,524, filed Nov. 17, 1980.

BACKGROUND OF THE INVENTION

Disposable absorbent structures such as disposable diapers, sanitary napkins and incontinence pads have met with increased commercial acceptance in recent years primarily because of their convenience. Many different constructions have been proposed and used and some have met with widespread commercial success in spite of certain inadequacies in functional properties.

One of the most serious prior art problems has been the inability to provide a suitable construction that can accept a large void of body fluids. This is particularly true of the adult incontinent whether the incontinent be active and working or ill and bedridden. Various attempts have been made to provide special structures to absorb a large body fluid void. These include U.S. Pat. No. 3,441,024 to H. J. Ralph, U.S. Pat. No. 3,747,602 to H. J. Ralph, U.S. Pat. No. 3,968,798 to K. C. Hokanson, and U.S. Pat. No. 4,067,366 to R. L. Johnson. While these various constructions were designed to assist the adult incontinent, the problem of providing an overall absorbent structure which will handle a full volume discharge of urine without leakage still remains.

Whether the incontinent be an adult or an infant, disposable structures generally have not accepted and held a full volume discharge of urine without leakage onto clothing. The present invention provides an absorbent structure which may be used as an infant diaper, an adult incontinence device, an incontinence pad or the like.

SUMMARY OF THE INVENTION

The present invention provides an absorbent structure to receive and contain body fluids, particularly urine, comprising a loosely-compacted, cellulosic fibrous batt having a moisture-impermeable backing sheet on one side and a fabric cover which covers at least the side of the absorbent batt opposite the backing sheet on the other side. The absorbent batt is substantially rectangular in shape and is provided with a reservoir which (1) has a capacity of at least 10 cc, (2) which covers at least one square inch of surface, (3) which is situated between the center and one transverse end of the substantially rectangular absorbent batt, (4) which covers less than about 25% of the surface area of the absorbent batt, and (5) is formed by compression of the cellulosic fibrous batt so that the depth of the reservoir is more than half the thickness of the absorbent batt.

In U.S. Pat. No. 4,184,498, there is provided a sanitary napkin which by its appearance would seem to be a structure which might be used for the deposit of urine and the containment thereof. It has been found, however, that a single depression such as is provided by the patent extending substantially the length of the structure does not contain a substantial discharge of urine when being worn in place. This is because the structure folds on the depression the entire length of the structure and fails to provide a substantial reservoir which retains its shape and consequently high volume of discharge. The single reservoir provided by the present invention does not permit the folding or collapse of the central portion behind the reservoir in such a way that liquid could leak. Instead, the reservoir of the present invention, as it is defined above, provides an absorbent structure which retains the reservoir substantially in its originally shaped state when the product is being used so that the entire absorbent structure is available for proper use without collapsing or folding to permit leakage. The absorbent structure of the present invention, when utilized either in a diaper-type structure or in a simple pad-type structure when worn between the legs of the wearer, attains a boat-like shape due to the compression on each side near the reservoir caused by the legs of the wearer. This boat-like shape keeps the reservoir available for substantially all of its holding capacity and keeps the ends and sides of the pad in a position such that leakage does not occur.

The absorbent structure may be incorporated in a disposable diaper such as for an infant or in an adult diaper with a larger liquid holding capacity. Furthermore, the absorbent structure may be incorporated in an incontinence pad. In each instance, the opening of the reservoir is placed in the void zone allowing immediate acceptance by the reservoir of the body fluid discharge. Generally, the discharge capacity of the reservoir is sufficient to hold at least 75% of the urine discharged in one second.

The reservoir is created by compression of the loosely-compacted, cellulosic fibers in the reservoir area. The compaction may be carried out by application of pressure in the shape desired for the reservoir. This may be done by a stamping-type operation or by an embossing roll or the like.

DETAILED DESCRIPTION OF THE INVENTION

Figure 1:
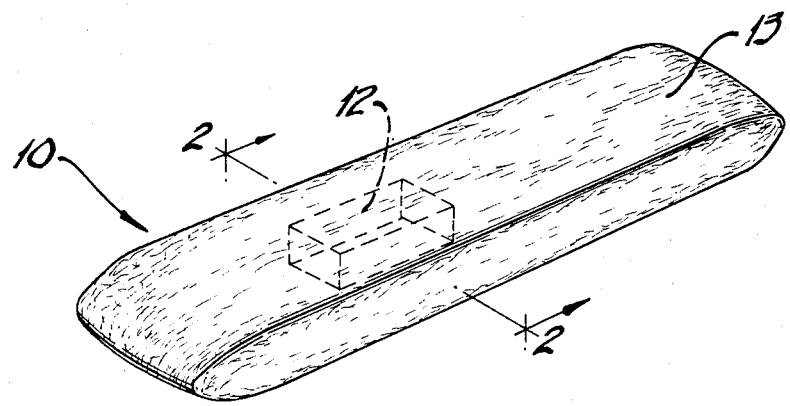
FIG. 1 is a perspective view of one embodiment of the present invention.

While this invention is susceptible of embodiment in many different forms, there is shown in the drawings, and herein will be described in detail, preferred embodiments of the invention and modifications thereof. It is understood that the present disclosure is to be considered as an exemplification of the principles of the invention and is not intended to limit the invention to the embodiments illustrated. The scope of the invention will be pointed out in the appended claims.

Figure 2:
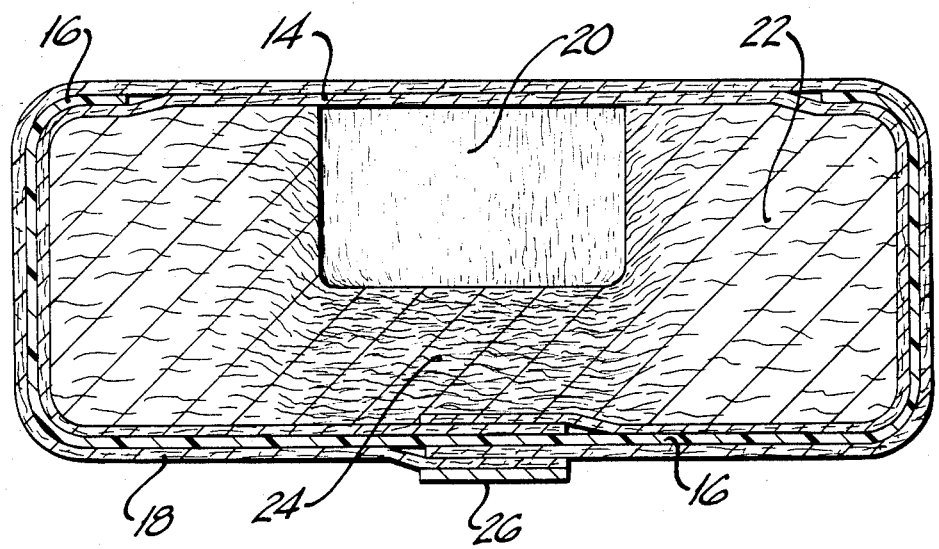
FIG. 2 is a cross-sectional view taken along line 2—2 of the embodiment of FIG. 1.

Referring to the drawings and particularly to FIG. 1, an absorbent structure 10 is provided with a reservoir 12 lying below the cover 13. The cover is a moisture-permeable nonwoven fabric. FIG. 2 shows the absorbent structure of FIG. 1 in cross-sectional view along line 2—2. The moisture-permeable exterior cover 18 completely wraps the absorbent structure. A moisture barrier 16 which is a moisture-impermeable backing sheet, covers the bottom area as well as both sides of the structure. Immediately adjacent the cellulosic batt 22 is a wrap of tissue 14. It may not be necessary to have a tissue wrapping the cellulosic batt but if the cellulosic batt is quite thick, such as an inch or more, it may be desirable to provide a tissue wrap to assist with maintenance of the desired shape of the absorbent structure. The cellulosic fibrous batt 22 is provided with a reservoir 20 and a densified fibrous region 24. The surface of the fibrous batt containing the opening of the reservoir 20 is placed toward the wearer with the opening in the void zone. A release liner 26 is removed to expose adhesive so as to secure the structure to the underwear of the wearer. This structure may be used as a urine pad or an incontinence pad.

Figure 3:
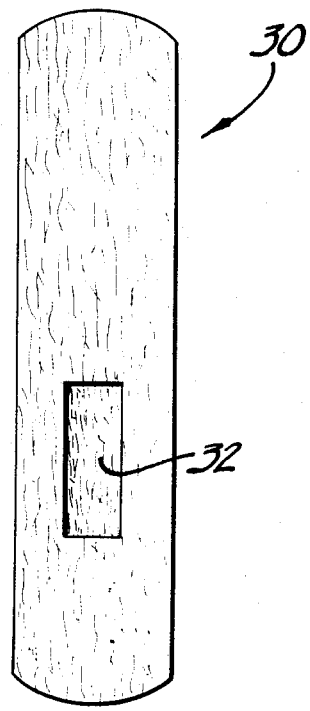
FIG. 3 is a top view of another embodiment of the present invention.
Figure 4:
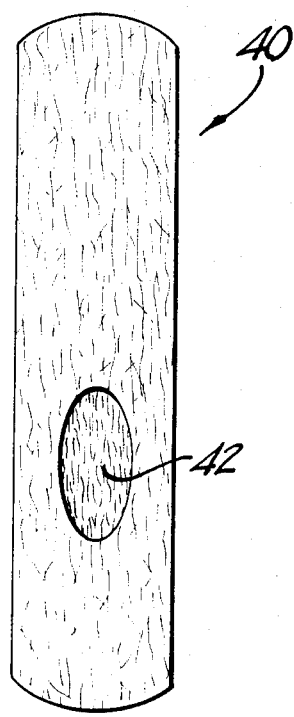
FIG. 4 is a top view of still another embodiment of the present invention.

FIGS. 3 and 4 are top views of typical cellulosic batts used in the absorbent structure of the invention. The cellulosic batt 30 contains a reservoir 32 having the shape of a rectangle. The reservoir is located nearer one end of the cellulosic batt 30, e.g., between the center and the end, to assist in location in the void zone of the wearer. In FIG. 4 a cellulosic batt 40 is provided with a reservoir 42 having an oval shape. Any desired shape and size may be used so long as the reservoir covers at least one square inch of surface and contains at least 10 cc in volume, but does not cover more than 25% of the surface.

Figure 5:
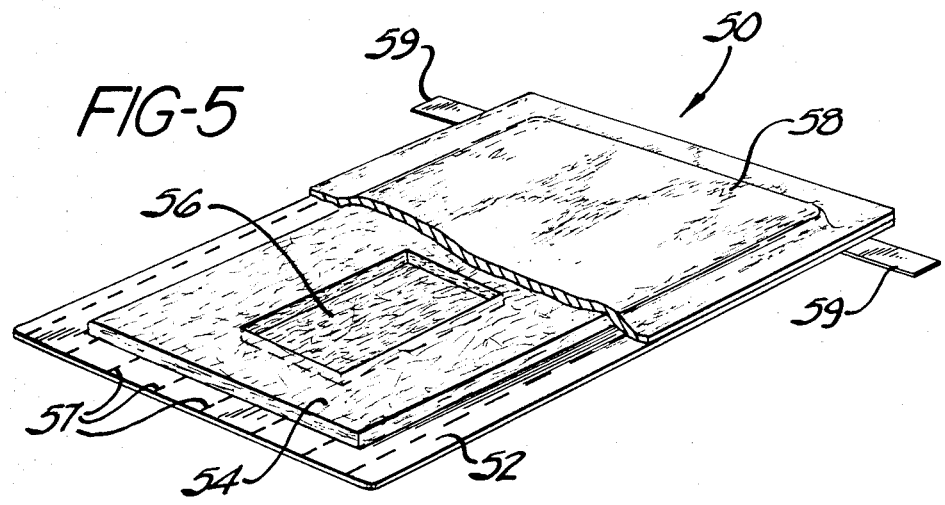
FIG. 5 is a perspective view of a disposable diaper utilizing the absorbent structure of the present invention.

Referring now to FIG. 5, a disposable diaper 50 is shown having a moisture-impermeable backing sheet 52. Superimposed upon the backing sheet 52 is a loosely-compacted, cellulosic fibrous batt 54. The fibrous batt contains a reservoir 56 created by compression or compaction of the fibers in that region. The cellulosic batt 54 is covered by a moisture-permeable facing 58 of nonwoven fabric. The facing and the backing are adhered in the margin regions. In addition, glue lines 57 are used to secure the fibrous batt to the backing. Tape tabs 59 are provided to secure the diaper about the wearer.

The loosely-compacted, cellulosic fibrous batt used in the absorbent structure of the present invention is formed from wood pulp fibers, rayon fibers, or cotton linters, or mixtures thereof. The batt is primarily held together by interfiber bonds requiring no added adhesive. In some instances, the batt may contain synthetic fusible fibers, such as polyethylene, polypropylene and the like. The batt is a low bulk density coherent web of loosely-compacted, cellulosic fibers preferably comminuted wood pulp fibers in the form of so-called "fluff".

The reservoir in the cellulosic batt is created by compressing the portion of the batt which it is desired become a reservoir so that the depth of the reservoir is more than half the thickness of the uncompressed batt. The base of the reservoir is a densified fibrous region wherein the fibers are compacted. The densified region quickly absorbs the body fluid and commences distribution of the fluid to other parts of the cellulosic batt. In addition, it may be desirable to provide a paper-like densified layer on the side of the batt opposite the reservoir. The paper-like densified layer is formed by a slight moistening of the surface of the batt followed by light compaction using the application of pressure. U.S. Pat. No. 3,017,304, Burgeni, provides such a densified layer in a loosel-compacted, cellulosic fibrous batt.

The cover provided on the absorbent structure of the present invention is a film or fabric having a high degree of moisture permeability. For example, the fabric may be polyester, polyethylene, polypropylene, nylon, rayon, or the like. Preferably, the fabric used for the cover is a lightweight fabric in the range of 0.3 to 5.0 oz. per square yard and with a density less than 0.2 gms/cc. The most suitable fabrics have unusually high elongation, loft, softness and drape characteristics. Films which are perforated or noncontinuous are also satisfactory. Though the cover is moisture-permeable, it is preferably of the type which after permeation of the moisture, prevents strike-back of the body fluid when the absorbent structure is approaching saturation.

The body of the cellulosic fibrous batt is substantially more wettable than the cover and tends to draw liquid away from the facing layer. Thus the void occurs and the cover is permeated and the liquid deposited in the reservoir. The individual fibers of the batt are extremely wettable and thus draw the liquid into the fibrous batt. The base of the reservoir fs a densified fibrous region wherein the capillary radius is quite small. Thus the capillary pressure is increased and the lfquid is rapidly distributed to portions of the cellulosic batt. The densified fibrous region at the base of the reservoir provides the maximum capillary pressure because it combines the very low contact angle of the fibers of the batt with the high density of the densified fibers.

The individual fibers of the batt are extremely wettable, generally having liquid-fiber contact angles below about 30° and approaching 20° in the optimum embodiment. The wickability or preferential absorptivity of the body of the batt for water is limited, however, by its low density which results in large effective capillary radii for the capillaries between adjacent fibers.

The pressure causing a liquid to enter a cylindrical capillary is expressed by the equation $$P = 2\nu \cos \theta / r$$

wherein
P is the capillary pressure,
$\nu$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and increases with narrower capillary radii so that narrower capillaries will draw liquid from wider ones.

The relative wickability between the cover layer and the body of the fibrous batt is affected by both the relative densities of the layers and the relative wettability of the individual fibers in each layer. The individual fibers of the batt have substantially smaller liquid-fiber contact angles than those of the cover layer overcoming the density difference and providing a substantial overall increase in capillary pressure to absorb liquid into the body of the batt.

A densified fiber layer such as that at the base of the reservoir provides the maximum capillary pressure because it combines the very low contact angle of the fibers of the batt with the high density (small capillary radius) of the densified fibers.

Thus when urine is voided into an area in the cover layer, it partially wets a small portion of the cover layer and is passed through the cover layer, almost instantaneously, to the reservoir. It then comes into contact with the body of the batt surrounding the reservoir and is preferentially absorbed into the body of the batt because of the enhanced wettability of the reservoir and particularly the base of the reservoir. The same is true when the body fluid is a menstrual fluid or other liquid exudate.

It will be understood by those skilled in the art that variations and modifications of the specific embodiments described above may be employed without departing from the spirit and scope of the invention as defined in the appended claims.

I claim:

1. An absorbent structure suitable for absorption of body fluids comprising a moisture-impermeable backing sheet; an absorbent, loosely-compacted, cellulosic fibrous batt, superimposed on said backing sheet; and a moisture-permeable fabric cover, covering at least the side of said absorbent batt opposite said backing sheet, said absorbent batt being provided with a reservoir having a capacity of at least 10 cc, covers at least one square inch but does not cover more than 25% of the surface of said absorbent batt said reservoir being situated between the center and one transverse end and being formed by compression of the cellulosic fibrous batt such that the depth of said reservoir is more than one-half the thickness of said absorbent batt.

2. The absorbent structure of claim 1 wherein the base of said reservoir is a densified region of the fibers of the fibrous batt.

3. An adult incontinence device substantially rectangular in shape comprising a moisture-impermeable backing sheet; an absorbent, loosely-compacted, cellulosic fibrous batt superimposed on said backing sheet; and a moisture-permeable fabric cover, covering at least the side of said absorbent batt opposite said backing sheet, said absorbent batt being provided with a reservoir covering at least one square inch of the surface of the batt but not more than 25% of the surface and having a capacity of at least 10 cc, said reservoir being situated between the center and one transverse end of the absorbent batt and being formed by compression of the cellulosic fibrous batt to provide a depth more than one-half the thickness of the absorbent batt.

4. The adult incontinence device of claim 3 wherein said backing sheet is provided with an adhesive layer which functions as an adhesive strip for securement of the device when worn.

5. A disposable diaper comprising a moisture-impermeable backing sheet; an absorbent, loosely-compacted, cellulosic fibrous batt, superimposed on said backing sheet; and a moisture-permeable facing superimposed on the side of the fibrous batt opposite said backing sheet, said absorbent batt being provided with a reservoir covering at least one square inch of the surface of the batt but not more than 25% of the surface and having a capacity of at least 10 cc, said reservoir being situated between the center and one transverse end of the absorbent batt and being formed by compression of the cellulosic fibrous batt to provide a depth in the reservoir of more than one-half the thickness of the absorbent batt.

6. The disposable diaper of claim 5 wherein the reservoir has as its base a densified fibrous region.

* * * * *